United States Patent [19]

Adelstein

[11] 4,116,963
[45] Sep. 26, 1978

[54] 3,3,3-TRIARYLALKYL-4-PHENYLALKYL-4-HYDROXY PIPERIDINES AND RELATED COMPOUNDS

[75] Inventor: Gilbert W. Adelstein, Evanston, Ill.

[73] Assignee: G.D. Searle & Co., Chicago, Ill.

[21] Appl. No.: 799,864

[22] Filed: May 23, 1977

[51] Int. Cl.$^2$ ............... C07D 211/48; C07D 401/06
[52] U.S. Cl. ..................... 260/293.69; 260/293.81; 260/293.84; 424/267; 424/263
[58] Field of Search ............... 260/293.84, 293.81, 260/293.69, 293.83

[56] References Cited

U.S. PATENT DOCUMENTS

| | | | |
|---|---|---|---|
| 3,438,991 | 4/1969 | Janssen | 260/293.8 |
| 3,462,444 | 8/1969 | Beckett et al. | 260/293.84 |
| 3,979,390 | 9/1976 | Sasajima et al. | 260/293.66 |
| 3,998,832 | 12/1976 | Adelstein | 260/293.71 |

FOREIGN PATENT DOCUMENTS 1,147,887  4/1969  United Kingdom ............... 260/293.61

*Primary Examiner*—Norma S. Milestone
*Attorney, Agent, or Firm*—John J. McDonnell

[57] ABSTRACT

The present invention encompasses compounds of the formula

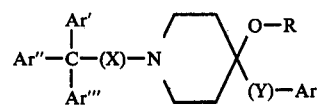

and the pharmaceutically acceptable acid addition salts thereof wherein R represents hydrogen, alkanoyl having 1 to 7 carbon atoms, or lower alkyl having 1 to 7 carbon atoms; X and Y represent alkylene having 1 to 3 carbon atoms and Ar, Ar', and Ar'' represent phenyl, halosubstituted phenyl, lower alkyl substituted phenyl wherein the lower alkyl contains 1 to 4 carbon atoms; and Ar''' represents phenyl, pyridyl, lower alkyl substituted phenyl wherein the lower alkyl contains 1 to 4 carbon atoms or halosubstituted phenyl. Compounds of the present invention are prepared by reaction of triarylalkanoyl halide with appropriately substituted piperidine followed by subsequent reduction of the resulting amide. Compounds of the present invention are potent antidiarrheal compounds with unexpected separation of antidiarrheal and central nervous system properties.

9 Claims, No Drawings

3,3,3-TRIARYLALKYL-4-PHENYLALKYL-4-HYDROXY PIPERIDINES AND RELATED COMPOUNDS

The present invention encompasses compounds of the formula

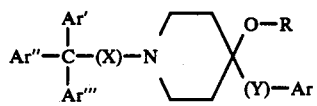

and the pharmaceutically acceptable acid addition salts thereof wherein R represents hydrogen, alkanoyl having 1 to 7 carbon atoms, or lower alkyl having 1 to 7 carbon atoms; X and Y represent alkylene having 1 to 3 carbon atoms and Ar, Ar', and Ar" represent phenyl, halosubstituted phenyl, lower alkyl substituted phenyl wherein the lower alkyl contains 1 to 4 carbon atoms; and Ar''' represents phenyl, pyridyl, lower alkyl substituted phenyl wherein the lower alkyl contains 1 to 4 carbon atoms or halosubstituted phenyl.

Thus, R representing alkanoyl having 1 to 7 carbon atoms, encompasses acetyl, propionyl, butyryl, pentanoyl, hexanoyl, heptanoyl, and branched chain isomers thereof and R representing lower alkyl encompasses methyl, ethyl, propyl, butyl, pentyl, hexyl, heptyl, and branched chain isomers thereof.

X and Y each independently represent methylene ethylene, propylene or isopropylene.

Ar, Ar' and Ar" are typically phenyl, chlorophenyl, bromophenyl, fluorophenyl, iodophenyl, tolyl, ethylphenyl, propylphenyl, isopropyl phenyl, butylphenyl, and branched chain butyl phenyls.

Ar''' in addition to the above phenyl derivatives is also 2, 3, or 4 pyridyl.

Thus, an embodiment of the present invention is a compound of the formula

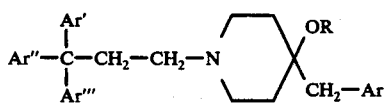

and the pharmaceutically acceptable acid addition salts thereof wherein Ar, Ar', Ar", Ar''', and R are as previously defined.

A compound of the formula

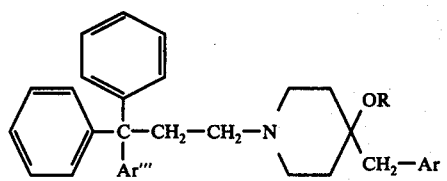

and the pharmaceutically acceptable acid addition salts thereof wherein Ar''', Ar, and R are as previously defined is likewise preferred.

More particular embodiments are of the formulae

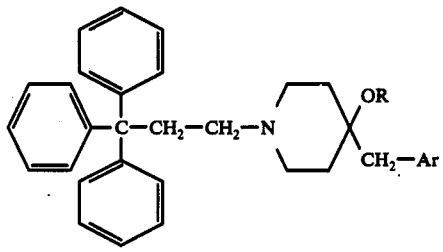

or

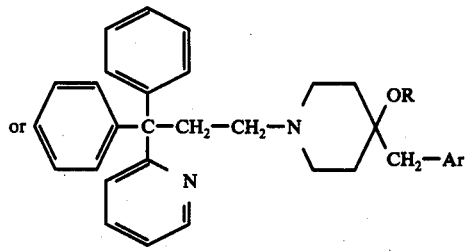

and the pharmaceutically acceptable acid addition salts thereof wherein R and Ar are as previously defined.

Compounds of the present invention are prepared according to the following scheme wherein Ar', Ar", Ar''', R, and Y are as previously defined and p is methylene or ethylene, or a direct bond from the triaryl carbon to the carbonyl carbon

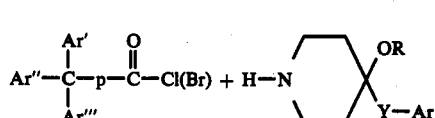

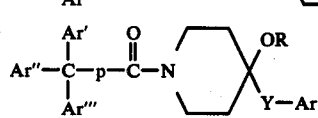

↓ LiAlH$_4$

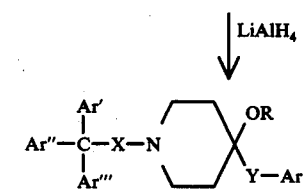

Alternatively, compounds can be prepared according to the following scheme

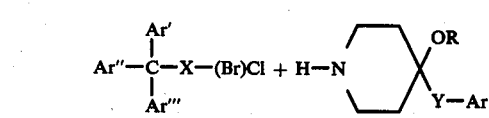

wherein the variables are as previously defined or

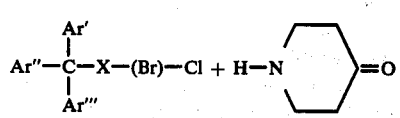

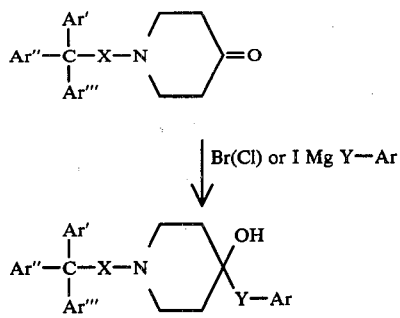

The hydroxy hydrogen is converted into an ester by reaction with an appropriate alkanoyl halide or into an ether by reaction with sodium hydride followed by an appropriate alkyl halide.

Useful techniques and intermediates are disclosed by S. Patai and Dayagi, J. Chem Soc 716(1962), D. Martensson and E. Nilsson, Acta Chem Scand. 19(3) 711 (1965) CA-63-6968h and H. Bochow Chem Ber 108, 3475 (1975). A wide variety of triphenylcarbinols are prepared by the reaction:

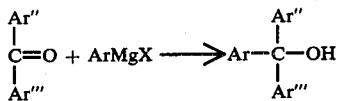

Equivalent to the compounds of both for the purposes of this invention are the pharmaceutically acceptable acid addition salts thereof. Such acid addition salts can be derived from a variety of organic and inorganic acids such as sulfuric, phosphoric, hydrochloric, hydrobromic, hydroiodic, sulfamic, citric, lactic, maleic, succinic, tartaric, cinnamic, acetic, benzoic, gluconic, ascorbic and related acids.

U.S. Pat. No. 3,998,832 describes 1-(3,3,3-triphenylpropyl)-4-hydroxy-4-phenylpiperidine compounds of the present invention differ in that the 4-phenyl is replaced with benzyl, phenethyl or phenpropyl. Unexpectedly, this structural change results in a remarkable separation of antidiarrheal and central nervous system affecting properties.

Thus, compounds of the present invention have an unexpectedly high antidiarrhea/analgesia therapeutic index.

The compounds herein described can be combined with pharmaceutically acceptable carriers to provide novel pharmaceutical compositions. The concentration of active ingredient in the composition is not critical, but is preferably 1–80%. These compositions can be administered orally, suitable forms for such administration including tablets, lozenges, capsules, dragees, pills, powders, solutions, suspensions and syrups. Acceptable pharmaceutical carriers are exemplified by gelatin capsules; sugars such as lactose or sucrose; starches such as corn starch or potato starch; cellulose derivatives such as sodium carboxymethyl cellulose, ethyl cellulose, methyl cellulose, or cellulose acetate phthalate; gelatin; talc; calcium phosphates such as dicalcium phosphates or tricalcium phosphate; sodium sulfate; calcium sulfate; polyvinyl pyrrolidone; acacia; polyvinyl alcohol; stearic acid; alkaline earth metal stearates suh as magnesium stearate; oils such as peanut oil, cottonseed oil, sesame oil; olive oil, corn oil, oil of theobroma; water; agar; alginic acid; and benzyl alcohol, as well as other non-toxic compatible substances used in pharmaceutical formulations.

The compounds of this invention can be used to produce an antidiarrheal effect in mammals by administering the instant novel compositions containing a therapeutically effective amount of the active ingredient. The term "therapeutically effective amount" is defined as the amount of active ingredient that will produce an antidiarrheal effect, i.e. which will reverse, inhibit or prevent diarrhea. For a particular subject, the amount of active ingredient to be used will vary with the subject involved, the severity of the diarrhea, and the particular active ingredient used. The therapeutically effective amount of a particularly active ingredient is determined by comparing its potency to that of a known standard such as diphenoxylate (Cutting's Handbook of Pharmacology, 4th edition, Appleton-Century Crafts, N.Y. at page 642.

The antidiarrheal effect of the compounds of the present invention are shown by the following test:

CECAL (Charcoal Meal Test)

Mice weighing 18–24 grams and previously fasted for 24 hours are each given orally 0.2 ml of a suspension containing 10% charcoal and 1% methylcellulose. The test compounds are administered intragastrically 1 hour prior to the charcoal meal. 3.5 Hours after administration of the meal the mice are sacrificed by cervical dislocation and the cecum is examined for the presence or absence of charcoal on an all or none basis. Each compound is tested at three dose levels (typically 30, 10, 3 mg/kg) in groups of 6 mice per dose level. Control groups of mice given vehicle only were run concurrently with each test group.

The assessment of the analgesic effect of the instant compounds was conducted in the mouse hot plate and tail clip tests.

Mouse Hot Plate Test

A mouse (adult male weighing 18–25 grams) is placed in a restraining cylinder on a hot plate with the temperature controlled at 55± 0.3° C. The reaction time of the mouse to lick a foot or jump is measured at 60, 40 and 20 minutes before and 30, 60, 90, and 120 minutes after administration of the test compound. The "normal" reaction time is measured as the median of the three pretreatment reaction times. A positive response consists of a reaction time greater than twice the normal time at any of the post treatment times. A dose of the test compound is considered active when 50 percent or more of the animals used show a positive response.

Tail Clip Test

A special clip is applied to the base of the tail of the mouse (adult male weighing 18–25 grams) and the time for the animal to turn around to bite at it is measured. The sensitivity of each mouse is determined one-half hour prior to drug administration. Only those mice attempting to bite the clip are included in the experiment. The test compund is then administered intraperitoneally and the response to placement of the clip is determined at 30, 60, 90, and 120 minutes after treatment. A response is considered positive if the animal takes more than 2 times the pre-drug time to bite at the clip at any of these time intervals. A test compound is considered active when 50 percent or more of the animals used show a positive response.

The therapeutic ratio of 1-(3,3,3-triphenylpropyl)-4-hydroxy-4-phenylpiperidine, U.S. Pat. No. 3,998,832 (I) and 1-(3,3,3-triphenylpropyl)-4-hydroxy-4-benzylpiperidine (II) with regard to antidiarrhea and analgesia (relative constipation specificity) is illustrated as follows.

| Compound No. | Cecal Test (CT) ED$_{50}$ mg/kg i.g. | Hot Plate (HP) ED$_{50}$ mg/kg k.g. | Tail Clip (TC) ED$_{50}$ mg/kg i.g. | Relative Constipation Specificity | |
|---|---|---|---|---|---|
| | | | | HP/CT | TC/CT |
| I | 0.39 | ≃3.0 | ≃3.0 | 7.6 | 7.6 |
| II | 0.6 | ≃400 | ≃400 | 667 | 667 |

The following examples describe in detail compounds illustrative of the present invention and methods which have been devised for their preparation. It will be apparent to those skilled in the art that many modifications, both of materials and methods, may be practiced without departing from the purpose and intent of this disclosure. Throughout the examples hereinafter set forth temperatures are given in degrees Centigrade (° C.), and relative amounts in parts by weight, except as otherwise noted.

EXAMPLE 1

3 Parts of triphenylpropionic acid are reacted with 1.2 parts by volume of thionyl chloride in 50 parts by volume of benzene by refluxing for 2 hours. The solvent is removed at reduced pressure. The residue is taken up in 25 parts by volume of benzene and added to a cooled mixture of 1.9 parts of 4-benzyl-4-hydroxy piperidine in 50 parts by volume of benzene and 2.1 parts of potassium carbonate in 2 parts of volume of water. A solid separates and is filtered and washed with cold ethanol and dried to provide 1-(3,3,3-triphenylpropionyl)-4-hydroxy-4-benzylpiperidine, melting at 150°–166° C. and having the following structural formula

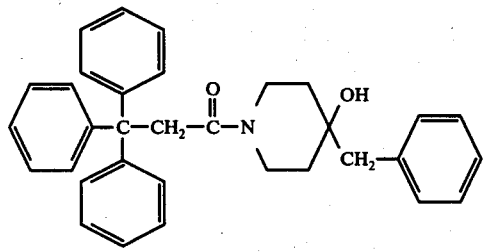

3 Parts of this amide and 3 parts of lithium aluminum hydride in tetrahydrofuran are refluxed overnight. The reaction mixture is treated with 3 parts by volume of water, 3 parts by volume of 15% sodium hydroxide, and 9 parts by volume of water and the resulting mixture is filtered. The filtrate is evaporated to form a semisolid which in turn is taken up in ethyl ether. The ether is gradually boiled away and replaced with hexane. On cooling there is a gradual oiling out. The hexane is decanted and the oil is taken up in ethyl ether and acidified with hydrochloric acid in isopropanol. The resulting solid is filtered and dried in vacuo to provide 1-(3,3,3-triphenylpropyl)-4-hydroxy-4-benzylpiperidine hydrochloride, melting at 267.5°–271° C. and having the following structural formula

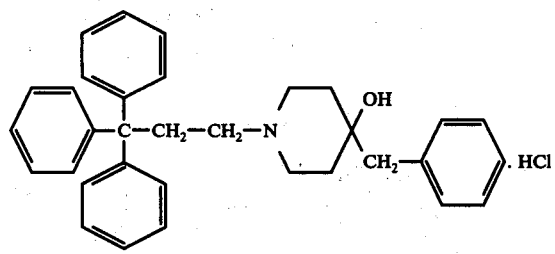

Recrystallization of a semisolid oil from the hexane layer from methanol and water provides 1-(3,3,3-triphenylpropyl)-4-hydroxy-4-benzylpiperidine, melting at 72°–74° C. and having the following formula

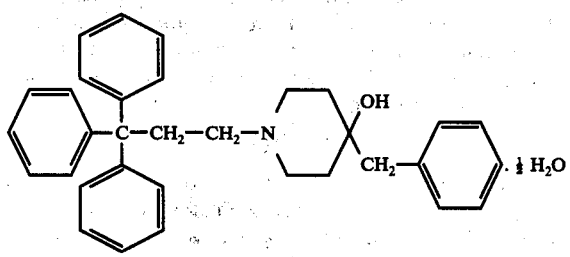

EXAMPLE 2

To a solution of p-chlorobenzylmagnesium chloride in ethyl ether (prepared from 16 parts of p-chlorobenzyl chloride and 3 parts of magnesium turnings in 100 parts of ethyl ether) is added dropwise a solution of 19 parts of N-benzyl-4-piperidone in 50 parts of ethyl ether, the reaction vessel being cooled in an ice bath during the addition. When the addition is complete, mixture is refluxed for 2 hours, cooled, and the Grignard decomposed with saturated ammonium chloride solution. Evaporation of the ethyl ether gives N-benzyl-4-p-chlorobenzyl-4-hydroxypiperidine.

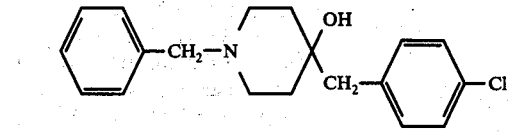

3 Parts of this amine and 0.5 parts of 5% in 100 parts of 3N-hydrochloric acid are shaken on a Parr shaker under hydrogen until uptake ceases. The catalyst is filtered off and the solvent evaporated to afford 4-p-chlorobenzyl-4-hydroxy piperidine hydrochloride.

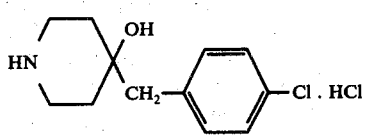

Following the procedure in Example 1 this piperidine is converted to 1-(3,3,3-triphenylpropyl)-4-hydroxy-4-p-chlorobenzylpiperidine, having the formula

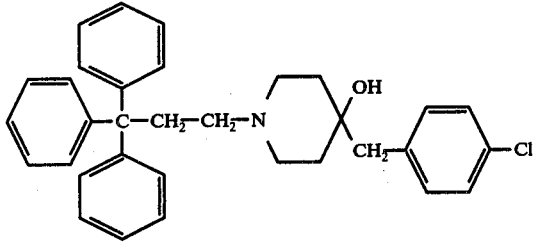

or the hydrochloride salt thereof.

In a similar manner 1-(3,3,3-triphenylpropyl)-4-hydroxy-4-p-bromobenzylpiperidine; 1-(3,3,3-triphenylpropyl)-4-hydroxy-4-p-fluorobenzylpiperidine; 1-(3,3,3-triphenylpropyl)-4-hydroxy-4-p-methylbenzylpiperidine; 1-(3,3,3-triphenylpropyl)-4-hydroxy-4-p-ethylbenzylpiperidine and the hydrochloride salts thereof are prepared.

EXAMPLE 3

Following the procedure in Example 2 using an equivalent amount of phenethylmagnesium chloride in place of p-chlorophenylmagnesium chloride provides 1-(3,3,3-triphenylpropyl)-4-hydroxy-4-phenethylpiperidine, having the following structural formula

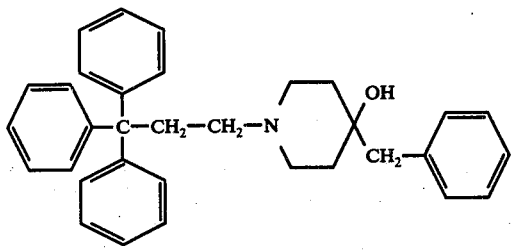

EXAMPLE 4

A solution of 3.0 parts of 1-(3,3,3-triphenylpropyl)-4-hydroxy-4-benzyl piperidine (obtained from the corresponding hydrochloride salt), 0.35 part of 50% sodium hydride suspension in mineral oil, and 70 parts by volume of 1,2-dimethoxyethane are heated at 37°–39° C. for 1.5 hours under nitrogen with stirring. The mixture is cooled to room temperature and 0.94 part of methyl iodide is added and the mixture is stirred at room temperature for 20 hours. The solvent is evaporated under reduced pressure and the residue is suspended in ether and filtered. The filtrate is washed with water, dried (Na$_2$SO$_4$) and evaporated under reduced pressure. The residue is put on an 0.5" column of Woelm silica gel and eluted with 2% ethanol in benzene under a pressure which maintains a flow rate of 8 ml/minute. The desired eluate evaporates and the residue dissolves in ether and is treated with an excess of hydrogen chloride in 2-propanol. The solid which forms is separated by filtration, washed with ether, and air-dried and then further recrystallized from a mixture of methanol and ether to give 1-(3,3,3-triphenylpropyl)-4-methoxy-4-benzyl piperidine hydrochloride having the following structural formula

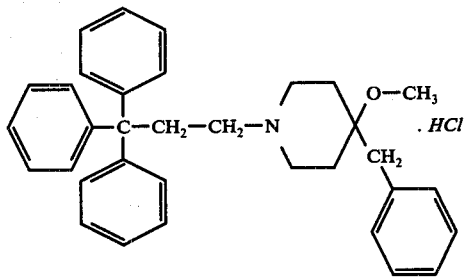

Following the above procedure using an equivalent quantity of n-hexylbromide in place of methyl iodide provides 1-(3,3,3-triphenylpropyl)-4-hexoxy-4-benzyl piperidine hydrochloride and having the following structural formula

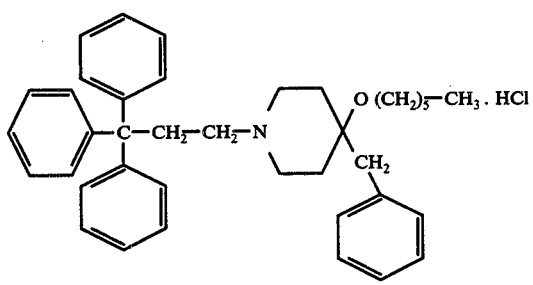

EXAMPLE 5

A mixture of 1.0 part of 1-(3,3,3-triphenylpropyl)-4-hydroxy-4-benzyl piperidine hydrochloride, 10 parts by volume of pyridine and 3.0 parts by volume of acetic anhydride is allowed to stand for 24 hours. Volatile material is removed under reduced pressure and the resulting residue is partitioned between dilute sodium hydroxide and ether. The ether layer is separated, washed with water, dried over sodium sulfate and then treated with an excess of a solution of hydrogen chloride in 2-propanol. The solid which forms is separated by filtration and then washed successively with ether, water, and ether, and then air-dried to give 1-(3,3,3-triphenylpropyl)-4-acetoxy-4-benzylpiperidine hydrochloride and having the following structural formula

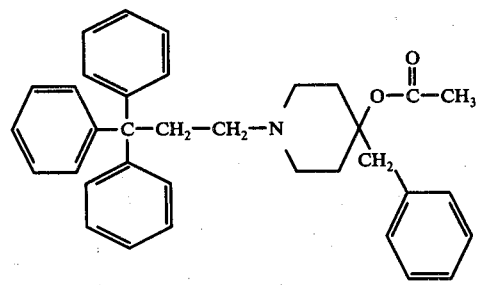

Replacement of acetic anhydride with 3.0 parts of propionic acid anhydride provides 1-(3,3,3-triphenylpropyl)-4-propionyloxy-4-benzylpiperidine hydrochloride.

EXAMPLE 6

A mixture of 2 parts of (p-chlorophenyl)diphenyl carbinol and 8 parts of malonic acid are heated at 170° for 31 hours. This mixture is cooled and then dissolved in hot ethanol, affording 3-p-chlorophenyl-3,3-diphenylpropionic acid. 1 Part of 3-(p-chlorophenyl)3,3-triphenylpropionic acid is then refluxed with 5 parts of thionyl chloride for 4 hours and the excess thionyl chloride is removed in vacuum to provide the crude 3-(p-chlorophenyl)3,3-diphenylpropionyl chloride. 9 Parts of this 3-(p-chlorophenyl)-3,3-triphenylpropionyl chloride are then reacted with 27.0 parts of 4-benzyl-4-hydroxypiperidine in the presence of 4 parts of triethylamine in benzene. The resulting amide is reduced with 5 parts of lithium aluminum hydride in ether at reflux for 2.5 hours. The reaction mixture is cooled and treated with 15% aqueous sodium hydroxide solution to decompose any unreacted lithium aluminum hydride. The reaction mixture is then filtered and washed with ether. The ether solution is evaporated to give an oil. This oil is then slurried in 10% HCl and extracted with ether. The aqueous phase which contains an insoluble oil is extracted with methylene chloride, and the methylene chloride extract dried over anhydrous sodium sulfate. Evaporation of this methylene chloride solution gives a solid which is taken up in acetone and precipitated with ether which affords 1-[3-p-chlorophenyl)-3,3-diphenylpropyl]-4-benzyl-4-hydroxypiperidine hydrochloride having the following structural formula

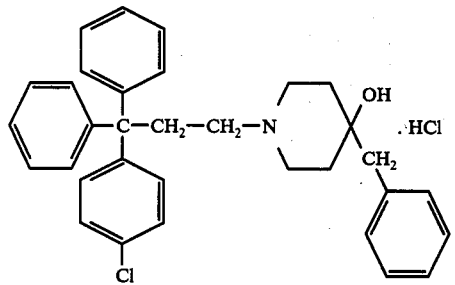

In a similar manner using appropriate reagents 1-(3-p-tolyl-3,3-diphenylpropyl)-4-benzyl-4-hydroxypiperidine and the hydrochloride salts thereof; 1-[3-(p-bromophenyl)-3,3-diphenylpropyl]-4-benzyl-4-hydroxypiperidine and the hydrochloride salts thereof; 1-[3-p-ethylphenyl)-3,3-diphenylpropyl]-4-benzyl-4-hydroxypiperidine and the hydrochloride salts thereof; and 1-[3,3-di(p-fluorophenyl)-3-phenylpropyl]-4-benzyl-4-hydroxypiperidine and the hydrochloride salts thereof.

EXAMPLE 7

To 23 parts of 1,4-dioxa-8-azaspiro[4.5]decane in 300 parts by volume of methanol is added 15 parts of ethylene oxide in methanol. The mixture is stirred at −20° C. for 3 hours and allowed to warm to room temperature. The solvent is removed under reduced pressure and the residue distilled to afford N-hydroxyethyl-1,4-dioxa-8-azaspiro[4.5]-decane. The corresponding tosylate is formed by reacting 16 parts of the alcohol in 75 parts of dry pyridine with 21 parts of p-toluenesulfonylchloride.

The mixture is stirred at 5° C. overnight and then poured into 300 parts by volume of ice water. The resulting solid is collected by filtration to afford the tosylate.

A solution of 25 parts of diphenyl-2-pyridyl methane in 200 parts of anhydrous ether is treated with 45 parts by volume of 2.3 molar n-butyllithium in hexane. The red mixture is stirred for 1 hour at room temperature and then 35 parts of the above tosylate in ether is added dropwise. The reaction mixture is stirred overnight at room temperature, quenched with water, the ethereal layer separated, dried over anhydrous sodium sulfate and evaporated to provide an intermediate of the formula

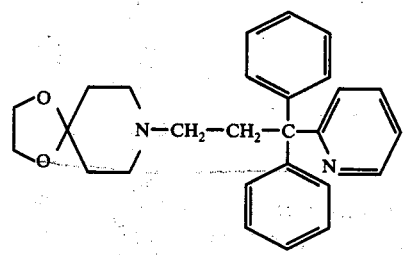

A solution of 1 part of this ketal in 5 parts of glacial acetic acid is added 0.1 part of sulfuric acid and the mixture is heated on a steam bath for 1 hour. The reaction mixture is poured into 50 parts of cold water to provide 1-[3,3-diphenyl-3-(2-pyridyl)propyl]-4-oxopiperidine. 3 Parts of this ketone in 20 parts by volume of ethyl ether and 5 parts by volume of 3 molar solution of benzylmagnesium bromide in ethyl ether are reacted under reflux for 4 hours. The mixture is cooled, quenched with water, and the ethereal layer is dried over anhydrous sodium sulfate. Removal of the ether provides 1-[3,3-diphenyl-3-(2-pyridyl)propyl]-4-benzyl-4-hydroxypiperidine, having the following structural formula

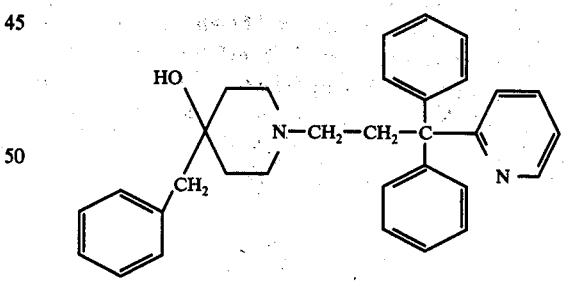

Extracting an ethereal solution of the above base with dilute hydrochloric acid separating the aqueous layer, and evaporating the water provides the corresponding hydrochloride salt. 1-[3,3-Diphenyl-3-(4-pyridyl)-propyl]-4-benzyl-4-hydroxypiperidine hydrochloride is prepared in substantially the same manner.

EXAMPLE 8

Initiating the procedure in Example 1 with equivalent quantities of triphenylacetic acid provides 1-(2,2,2-triphenylethyl)-4-hydroxy-4-benzylpiperidine, having the following chemical structure

What is claimed is:

1. Compounds of the formula $$\text{Ar''}-\underset{\underset{\text{Ar'''}}{|}}{\overset{\overset{\text{Ar'}}{|}}{\text{C}}}-(X)-N\begin{pmatrix}\text{O-R}\\ \text{(Y)-Ar}\end{pmatrix}$$

and the pharmaceutically acceptable acid addition salts thereof wherein R represents hydrogen, alkanoyl having 1 to 7 carbon atoms or lower alkyl having 1 to 7 carbon atoms; X and Y represent alkylene having 1 to 3 carbon atoms and Ar, Ar', Ar" represent phenyl, halosubstituted phenyl, lower alkyl substituted pheynyl wherein the lower alkyl contains 1 to 4 carbon atoms; and Ar''' represents phenyl, pyridyl, lower alkyl substituted phenyl wherein the lower alkyl contains 1 to 4 carbon atoms or halosubstituted phenyl.

2. A compound according to claim 1 of the formula $$\text{Ar''}-\underset{\underset{\text{Ar'''}}{|}}{\overset{\overset{\text{Ar'}}{|}}{\text{C}}}-\text{CH}_2-\text{CH}_2-N\begin{pmatrix}\text{O-R}\\ \text{M-Ar}\end{pmatrix}$$

and the pharmaceutically acceptable acid addition salts thereof wherein R is hydrogen or alkanoyl having 1 to 7 carbon atoms, or lower alkyl having 1 to 7 carbon atoms; M is alkylene having 1 to 3 carbon atoms and Ar, Ar', and Ar" are phenyl, halosubstituted phenyl, lower alkyl substituted phenyl wherein the lower alkyl contains 1 to 4 carbon atoms; and Ar''' is phenyl, pyridyl, lower alkyl substituted phenyl wherein the lower alkyl contains 1 to 4 carbon atoms or halosubstituted phenyl.

3. A compound according to claim 1 of the formula $$\text{Ar''}-\underset{\underset{\text{Ar'''}}{|}}{\overset{\overset{\text{Ar'}}{|}}{\text{C}}}-\text{CH}_2-\text{CH}_2-N\begin{pmatrix}\text{OR}\\ \text{CH}_2-\text{Ar}\end{pmatrix}$$

and the pharmaceutically acceptable acid addition salts thereof wherein R is hydrogen or alkanoyl having 1 to 7 carbon atoms, or lower alkyl having 1 to 7 carbon atoms; Ar, Ar', and Ar" are phenyl, halosubstituted phenyl, lower alkyl substituted phenyl wherein the lower alkyl contains 1 to 4 carbon atoms; and Ar''' is phenyl, pyridyl, lower alkyl substituted phenyl wherein the lower alkyl contains 1 to 4 carbon atoms or halosubstituted phenyl.

4. A compound according to claim 1 of the formula and the parmaceutically acceptable acid addition salts thereof wherein R is hydrogen or alkanoyl having 1 to 7 carbon atoms, or lower alkyl having 1 to 7 carbon atoms; Ar''' represents phenyl or pyridyl and Ar represents phenyl, or pyridyl and Ar represents phenyl, halosubstituted phenyl, lower alkyl substituted phenyl wherein the lower alkyl contains 1 to 4 carbon atoms.

5. A compound according to claim 1 which is 1-(3,3,3-triphenylpropyl)-4-hydroxy-4-benzylpiperidine.

6. A compound according to claim 1 which is 1-(3,3,3-triphenylpropyl)-4-hydroxy-4-benzylpiperidine hydrochloride.

7. A compound according to claim 1 which is 1-(3,3,3-triphenylpropyl)-4-hydroxy-4-p-chlorobenzylpiperidine.

8. A compound according to claim 1 which is 1-(3,3,3-triphenylpropyl)-4-hydroxy-4-p-methylbenzylpiperidine.

9. A compound according to claim 1 which is 1-[3,3-3(2-pyridyl)propyl]-4-benzyl-4-hydroxypiperidine.

* * * * *